United States Patent [19]

Imamura et al.

[11] Patent Number: 4,960,958
[45] Date of Patent: Oct. 2, 1990

[54] CATALYSTS FOR CATALYTIC PYROLYSIS OF PHENOL DISTILLATION RESIDUE AND PROCESS FOR RECOVERING USEFUL SUBSTANCES BY PYROLYSIS THE SAME

[75] Inventors: Tetsuo Imamura; Tatsuo Shirahata, both of Chiba; Kichiro Shoji, Oosaka, all of Japan

[73] Assignee: Mitsui Petrochemical Industries, Ltd., Tokyo, Japan

[21] Appl. No.: 410,811

[22] Filed: Sep. 22, 1989

Related U.S. Application Data

[62] Division of Ser. No. 178,411, Apr. 6, 1988.

[30] Foreign Application Priority Data

Apr. 9, 1987 [JP] Japan .................................. 62-87638
Apr. 9, 1987 [JP] Japan .................................. 62-87639

[51] Int. Cl.$^5$ ...................... C07C 37/00; C07C 37/68; C07C 37/74
[52] U.S. Cl. .................................. 568/806; 568/754; 585/838
[58] Field of Search ............... 568/754, 806; 502/236; 585/838

[56] References Cited

U.S. PATENT DOCUMENTS

| | | | |
|---|---|---|---|
| 2,073,398 | 3/1937 | Chesny | 23/201 |
| 2,757,209 | 7/1956 | Joris | 568/754 |
| 2,910,511 | 10/1959 | Joris | 568/754 |
| 3,454,653 | 7/1968 | Larson | 568/754 |
| 3,977,999 | 8/1976 | Erickson | 502/355 X |
| 4,002,653 | 1/1977 | Reuter et al. | 502/350 X |
| 4,444,899 | 4/1984 | Yamada et al. | 502/355 X |
| 4,522,709 | 6/1985 | Aldag et al. | 502/350 X |
| 4,637,995 | 1/1987 | DeAngelis et al. | 502/263 X |

FOREIGN PATENT DOCUMENTS

| 1121621 | 11/1962 | Fed. Rep. of Germany | 568/754 |
|---|---|---|---|
| 50-39831 | 1/1975 | Japan | 502/263 |

OTHER PUBLICATIONS

Chemical Abstracts, vol. 89, No. 19, Nov. 6, 1978, p. 546, Abstract #163263q.

*Primary Examiner*—Werren B. Lone
*Attorney, Agent, or Firm*—Nixon & Vanderhye

[57] ABSTRACT

The catalysts for use in pyrolytic decomposition of the phenol distillation residue in accordance with the present invention are used in pyrolytically decomposing a distillation residue resulting from the separation by distillation of cumene, phenol and acetone from a reaction mixture obtained by oxidizing cumene with molecular oxygen followed by acid cleavage, and the present catalysts are characterized by comprising oxygen containing metallic compounds having a particle diameter of 0.002–100 μm.

Furthermore, the processes for recovering useful substances from a phenol distillation residue containing the same in accordance with the present invention are characterized by allowing said phenol distillation residue to undergo pyrolytic reaction at a temperature of 200°–350° C., preferably 250°–300° C., in the presence of the above-mentioned oxygen containing metallic compound catalysts having a particle diameter of 0.002–100 μm, thereby recovering the useful substance such as cumene, phenol and the like from the phenol distillation residue.

4 Claims, No Drawings

CATALYSTS FOR CATALYTIC PYROLYSIS OF PHENOL DISTILLATION RESIDUE AND PROCESS FOR RECOVERING USEFUL SUBSTANCES BY PYROLYSIS THE SAME

This is a division of application Ser. No. 07/178,411, filed Apr. 6, 1988.

TITLE

FIELD OF THE INVENTION

This invention relates to catalysts for use in recovering useful substances, such as cumene, α-methylstyrene, phenol in high yields by pyrolysis reaction of a distillation residue from a reaction mixture containing by-products resulting from a process for preparing phenol and acetone by oxidation of cumene with molecular oxygen followed by acid-cleavage, and also to a process for recovering said useful substances by using said catalysts from a resIdue resulting from distillation of phenol and acetone from a reaction mixture obtained in said oxidation of cumene with molecular oxygen followed by acid-cleavage.

BACKGROUND OF THE INVENTION

Phenol is known as an intermediate widely used for the synthesis of synthetic resins, surfactants, medicines and the like. Various processes are known as methods of preparing such phenol as referred to above, however, a method which has been mainly adopted therefor is a so-called cumene process wherein phenol and acetone are prepared by oxidizing cumene with molecular oxygen to cumene hydroperoxide which is then cleavaged with acid to phenol and acetone.

However, where phenol is prepared by the cumene process which comprises oxidizing cumene with molecular oxygen, it is inevitable that dimethyl phenyl carbinol, acetophenone, α-methylstyrene, α-methylstyrene dimer, cumyl phenol and the like are formed as by-products in the course of oxidation reaction and consequently the resulting reaction mixture contains, in addition to phenol and acetone, such by-products as mentioned above. Accordingly, a residue (hereinafter sometimes called a phenol distillation residue), which is obtained after the separation by distillation of cumene, phenol and acetone from the above-mentioned resulting reaction mixture, contains such by-products as dimethylphenyl carbinol, acetophenone, α-methylstyrene, α-methylstyrene dimer, etc. Recovery of useful substances by converting these by-products is a matter of importance from the standpoint of reduction of the production costs of phenol by the cumene process.

Heretofore, the recovery of such useful substances as cumene, α-methylstyrene and phenol from this phenol distillation residue has been practiced by pyrolytically decomposing the phenol distillation residue, followed by distillation or the like. In the prior art process which comprises pyrolytically decomposing the phenol distillation residue, however, there were involved such problems that it takes a long period of time to complete the decomposition and, moreover, recoveries of cumene, α-methylstyrene and phenol are low.

For the purpose of solving such problems as mentioned above, Japanese Patent Publication No. 36892/1984 discloses processes for recovering useful substances such as cumene, α-methylstyrene and phenol from the phenol distillation residue resulting from a process for preparing phenol by the cumene process wherein cumene, phenol and acetone are separated by distillation, which processes are characterized in that said phenol distillation residue is pyrolytically decomposed in the presence of alumina catalysts such as α-alumina and the like or silica-alumina catalysts such as silica alumina, acid clay, synthetic zeolite and the like, or in the presence of these catalysts mentioned above and acids.

According to examples concretely disclosed in Japanese patent publication No. 36892/1984 cited above, however, it has been found that the processes embodied in the examples involve such problems that because the silica-alumina catalysts used have a large particle diameter such as 110–500 μm and the $Al_2O_3:SiO_2$ ratio of from 10:90 to 50:50 and, moreover, the reaction temperature employed is elevated finally up to 340°–345° C., the recovery of α-methylstyrene from dimethylphenyl carbinol, α-methylstyrene dimer, o-cumyl phenol and p-cumyl phenol is as high as 70–100%, whereas the recovery of phenol therefrom is markedly low as low as 3–30%.

OBJECT OF THE INVENTION

The present invention is intended to solve such problems associated with the prior art as mentioned above, and an object of the invention is to provide catalysts for use in pyrolitic decomposition of the phenol distillation residue and also processes for recovering useful substances from said phenol distillation residue, said phenol distillation residue being a liquid residue of distillation obtained at the tIme when a process for preparing phenol and acetone is carried out, which process comprises oxidizing cumene with molecular oxygen to cumene hydroperoxide which is then subjected to acid cleavage, and separating cumene, phenol and acetone by distillation from the resulting reaction mixture.

SUMMARY OF THE INVENTION

The catalysts for use in pyrolytic decomposition of the phenol distillation residue in accordance with the present invention are used in pyrolytic decomposition of a distillation residue which is resulted from the separation by distillation of cumene, phenol and acetone from a reaction mixture obtained by oxidizing cumene with molecular oxygen to cumene hydroperoxide which is then subjected to acid cleavage, and the catalysts of the invention are characterized in that they comprise oxygen containing metallic compounds having a particle diameter of 0.002–100 μm.

Further, the processes for recovering useful substances from the phenol distillation residue in accordance with the present invention, said phenol distillation residue resulting from the separation by distillation of cumene, phenol and acetone from a reaction mixture obtained by oxidizing cumene with molecular oxygen to cumene hydroperoxide followed by acid cleavage, are characterized in that said phenol distillation residue is allowed to undergo pyrolitic reaction at a temperature of 200°–350° C., preferably 250°–310° C., in the presence of catalysts comprising oxygen containing metallic compounds having a particle diameter of 0.002–100 μm, thereby recovering the useful substances such as cumene, phenol and α-methylstyrene.

By virtue of pyrolytically decomposing the phenol distillation residue by the use of the catalysts for use in pyrolytic decomposition of phenol distillation residue of the present invention, it is possible to recover in high yields not only cumene and α-methylstyrene but also phenol from said phenol distillation residue, and accordingly the present catalysts greatly contribute to the reduction of production costs of phenol.

DETAILED DESCRIpTION OF THE INVENTION

The catalysts for use in pyrolytic decomposition of the phenol distillation residue and &he processes for recovering useful substances from the phenol distillation residue by using said catalysts in accordance with the present invention are illustrated hereinafter in detail.

The catalysts for use in pyrolytic decomposition of the phenol distillation of the present invention are used in catalytic pyrolysis of a residue (phenol distillation residue) resulting from the separation by distillation of cumene, phenol and acetone from a reaction mixture obtained at the time when phenol and acetone are prepared by oxidizing cumene with molecular oxygen to cumene hydroperoxide, followed by cleavage with acids or the like.

More particularly, the catalysts of the present invention are used in catalytic pyrolysis of the phenol distillation residue which is resulted from the separation by distillation of cumene, phenol and acetone from a reaction mixture obtained by oxidizing cumene with molecular oxygen to cumene hydroperoxide, followed by acic cleavage, whereby such useful substances as phenol, cumene and α-methylstyrene are recovered therefrom, as shown by the following reaction formula.

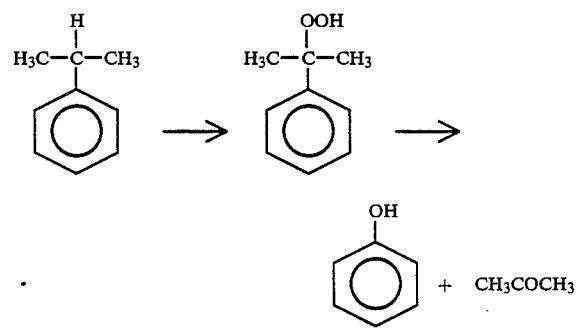

The catalysts for use in pyrolytic decomposition of the phenol distillation residue in accordance with the present invention are illustrated below in more detail.

In the distillation residue resulting from the separation by distillation of cumene, phenol and acetone from a reaction mixture obtained by oxidizing cumene with molecular oxygen to cumene hydroperoxide followed by acid cleavage, there are contained as by-products large amounts of dimethylphenyl carbinol shown below, α-methylstyrene dimer, o-cumyl phenol, p-cumyl phenol, acetophenone or other high boiling products.

Dimethylphenyl carbinol

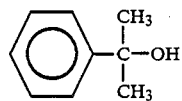

The catalysts for use in pyrolytic decomposition of the phenol distillation residue are added to such phenol distillation residue as containing the above-exemplified by-products. The present catalysts comprise oxygen containing metallic compounds having a particle diameter of 0.002-100 μm. pyrolytic decomposition of the phenol distillation residue using the present catalysts is carried out at a temperature of 200°-350° C., preferably 250°-310° C.

The oxygen containing metallic compound catalysts used in the present invention have a particle diameter of 0.002-100 μm, preferably 0.01-50 μm more preferably 0.02-10 μm, and said oxygen containing metallic compounds may assume such a form as metallic oxide, metallic hydroxide or metallic hydrated oxide. Such oxygen containing metallic compounds may contain either one metal or composite of two or more metals.

Such oxygen containing metallic compound catalysts as mentioned above may be prepared by methods generally adopted for the preparation of ultrafine oxygen containing metallic compounds, which methods include, for example, those as will be illustrated hereinafter.

1. Vapor phase reaction method
  (a) The method wherein alkyl metallic compounds, metallic chlorides or metals are decomposed with oxygen and water under the circumstances of water vapor and high temperature, thereby yielding corresponding metallic oxides or metallic hydroxides.
  (b) The method wherein metallic compounds (e.g. metallic chlorides) are fed to hydrogen-oxygen flame or hydrocarbon-oxygen flame, thereby yielding corresponding metallic oxides.
  (c) The method wherein metallic compounds (e.g. metallic halides) are heated by thermoplasma laser or electron beam, thereby yielding corresponding metallic oxides.

2. Liquid phase reaction method
  (a) The method wherein a precipitant is added to a mixed metallic salt solution to prepare a precipitate in which the metallic salts have been homogeneously mixed together, and this precipitate is then thermally decomposed to yield corresponding metallic oxides.
  (b) The method wherein a metallic salt solution is hydrolyzed to precipitate a metallic hydroxide or a metallic hydrated oxide, and the resulting precipitate is then converted into a corresponding metallic oxide.
  (c) The method Wherein urea is added to a solution of phosphate, oxalate or sulfate of a metal, the solution is heated to homogeneously precipitate the salt by the action of ammonia formed by decomposition of urea, and &he precipitate obtained is thermally decomposed to a corresponding metallic oxide.
  (d) The method wherein a metallic salt solution is atomized in a high temperature atmosphere and thereby to instantaneously cause the evaporation of the solution and thermal decomposition of the metallic salt, whereby a corresponding metallic oxide is obtained.
  (e) The method wherein a precipitate (precursor) containing solution obtained in the above-mentioned method (a),(b) or (c) is added to a phenol distillation residue, and then evaporating a solvent by heating the resulting mixture to yield a corresponding fine metallic oxide Metals which constitute the oxygen containing metallic compound catalysts of the present invention are preferably those belonging to the third and four&h periods of the periodic table but excluding alkali metals therefrom, and particularly favorable are Mg, Al, Si, Zn, Ti, V, Cr, Mn, Fe, Co, Ni and Cu.

Of these metals exemplified above, aluminum may be produced by methods generally adopted for the production of high purity alumina, which methods include, for example, those as mentioned below.

(1) The method which involves thermal decomposition of ammonium alum.

$Al_2(SO_4)_3 + (NH_4)_2SO_4 + 24H_2O \rightarrow 2NH_4Al(SO_4)_2 \cdot 12H_2O$ $2NH_4Al(SO_4)_2 12H_2O \rightarrow Al_2O_3 + 2NH_3 + 4SO_3 + 25H_2O$ (2) The method which involves hydrolysis of organoaluminum.

$2AlR_3 + 6H_2O \rightarrow Al_2O_3 \cdot 3H_2O + 6RH$ $2Al(OR)_3 + 6H_2O \rightarrow Al_2O_3 \cdot 3H_2O + 6ROH$ (3) Ethylene chlorohydrin method.

$2NaAlO_2 + 2ClCH_2CH_2OH \rightarrow Al_2O_3 \cdot nH_2O + 2C_2H_4O + 2NaCl$ (4) The method which involves thermal decomposition of ammonium aluminum carbonate.

$8NH_4HCO_3 + 2NH_4Al(SO_4)_2 \rightarrow 2NH_4AlO(OH)HCO_3 + 4(NH_4)_2SO_4 + 6CO_2 + 2H_2O$ $NH_4AlO(OH)HCO_3 \rightarrow Al_2O_3$ (5) The method relying on an improved Baeyer method by which alumina is usually obtained from bauxite, wherein alumina impurities are removed at the time when aluminum hydroxide is deposited followed by firing.

(6) The method which comprises causing spark discharge among aluminum pellets in water, thereby yielding alumina hydrate Which is then thermally decomposed.

In the present invention, such ultrafine oxygen containing metallic compound catalysts as illustrated above are directly added to the phenol distillation residue, or such precursors capable of forming ultrafine oxygen containing metallic compound catalysts in the phenol distillation residue, for example as aluminum phenoxide, titanium isopropoxide may be added to said phenol distillation residue, wherein the precursors are subjected to the aforementioned treatment such as hydrolysis or the like, thereby forming the desired ultrafine oxygen containing metallic compound catalysts.

Of the two procedures mentioned above, preferred is the latter procedure wherein the ultrafine metallic compound catalysts are formed in the pyrolysis. According to this latter procedure, the ultrafine metallic compound catalysts can be formed by hydrolysis of the metallic compounds as precursors with water formed by dehydration of by-products such as dimethylphenyl carbinol and the like present in the phenol distillation residue, which are liable to dehydration. In this procedure, the amount of the catalyst used can be minimized, the pyrolitic reaction can be carried out in a continuous manner and, moreover, there is no need for consideration of the catalyst life.

In the case where the ultrafine oxygen containing metallic compounds are formed by hydrolysis of metallic salts in the phenol distillation residue in the manner as mentioned above, precursors used for forming the oxygen containing metallic compound catalysts include metallic chlorides, metallic bromide, metallic nitrate, and organometallic compounds.

The metallic chlorides used as precursors include concretely aluminum chloride, Iron chloride, tItanIum tetrachloride, titanium trichloride, cobalt chloride, nickel chloride, manganese chloride, chromium chloride, zinc chloride, vanadium chloride, calcium chloride.

The metallic bromide include concretely aluminum bromide, iron(I) bromide, iron(II) bromide, calcium bromide, cobalt bromide, manganese bromide, copper bromide; nickel bromide and zinc bromide.

The metallic nitrate include concretely aluminum nitrate, iron(I) nitrate, iron(II) nitrate, calcium nitrate, cobalt nitrate, manganese nitrate, copper nitrate, nickel nItrate and zinc nitrate.

The organometallic compounds include concretely (i) organo aluminum compounds such as aluminum acetyl acetate, triethyl aluminum, aluminum isopropoxide and aluminum phenoxide, (ii) organo titanium compounds such as tetra-n-butyl orthtitanium, tetra-isopropyl orthtitanium and tetra-octadecyl orthtitanium, (iii) orqano magnesium compounds such as magnesium acetyl acetate, n-butyl magesium chloride, phenyl magesium bromide and (iv) other organometallic compounds such as chromium acetate, cobalt acetate, copper acetate, Ion acetate and cobalt phthalocyamine.

The catalysts of the present invention may also be used for pyrolytic decomposition of such residue similar to the phenol distillation residue that (i) a residue which is obtained after a separation by distillation of cymene, cresol from a reaction mixture obtained by oxidation of cymene with molecular oxygen, followed by acid-cleavage (ii) a residue which is obtained after a separation by distillation and crystallization of diisopropyl benzene, hydroquinone, resorcin from a reaction mixture obtained by oxidation of diisopropyl benzene with molecular oxygen followed by acid-cleavage and (iii) a residue which is obtained after a separation by crystallization and distillation of phenol and bisphenol A (2,2-bis(4-hydroxyphenyl)propane) from a reaction mixture obtained by condensation of phenol and acetone.

These precursors are preferably used after dissolving them in organic solvent, for example, anhydrous hexane, phenol, methanol, ethanol, isopropanol and dissolving water.

The pyrolysis reaction of the phenol distillation residue using the ultrafine oxygen containing metallic compound catalysts mentioned above may be .carried out either batchwise or continuously. The ultrafine oxygen containing catalysts are used in an amount of 0.1–50,000 ppm, preferably 10–1,000 ppm by weight based on the weight of the phenol distillation residue.

The above-mentioned pyrolysis reaction of the phenol distillation residue using the ultrafine oxygen containing metallic compound catalysts is usually carried out at 400 mmHg to 4 kgf/cm$^2$ abs, preferably under ordinary pressure, though the reaction may be carried out either subatmospheric or atmospheric pressure conditions or under pressure conditions. The reaction time employed is usually 2–15 hours, preferably 4–12 hours, though it varies greatly depending on the reaction temperature employed.

When the phenol distillation residue is pyrolitically decomposed in &he presence of the oxygen containing metallic compound catalysts having a particle diameter of 0.002–100 μm, dimethylphenyl carbinol o-, p-cumyl phenol and α-methylstyrene dimer contained in the phenol distillation residue are converted in high selectivity into α-methylstyrene. That is, dimethylphenyl carbinol is dehydrated to α-methylstyrene, and α-methylstyrene dimer is depolymerized to α-methylstyrene. Further, o-cumyl phenol and p-cumyl phenol contained also are decomposed to α-methylstyrene and phenol.

The catalysts of the present invention may also be used for pyrolytic decomposition of such residue similar to the phenol distillation residue that (i) a residue which is obtained after a separation by distillation of cymene, cresol from a reaction mixture obtained by oxidation of cymene with molecular oxygen, (ii) a residue which is obtained after a separation by distillation and crystallization of diisopropyl benzene, hydroquinone, resorcin from a reaction mixture obtained by oxidation of diisopropyl benzene with molecular oxygen and (iii) a residue which is obtained after a separation by crystallization and distillation of phenol and bisphenol A (2,2-bis(4-hydroxyphenyl)propane) from a reaction mixture obtained condensation of phenol and acetone.

EFFECT OF THE INVENTION

By virtue of carrying out pyrolitic decomposition of the phenol distillation residue by the use of the catalysts for use in pyrolitic decomposition of the phenol distillation residue in accordance with the present invention, not only cumene and α-methylstyrene but also phenol can be recovered in high yields from the phenol distillation residue.

Accordingly, when phenol is prepared by the cumene process, the use therein the catalysts of the present invention greatly contributes to reducing the production costs of the phenol.

The present invention is illustrated below with reference to examples, but it should be construed that the invention is in no way limited to those examples.

Example 1

Into a 200 ml four neck flask equipped with a stirring device, a cooling pipe, a nitrogen blowing head and a temperature detector was charged 100 g of a phenol distillation residue (composition by weight: 10-20% acetophenone, 10-20% dimethylphenyl carbinol, 10-30% phenol, 10-20% p-cumyl phenol, 10-20% α-methylstyrene dimer, 5-10% o-cumyl phenol, and the remainder as heavy substances), said phenol distillation residue resulting from the separation by distillation of most of acetone, cumene, α-methylstyrene and phenol from a reaction mixture obtained by the cumene process, and further were added thereto 0.4 g (titanium tetrachloride concentration 5% by weight) of an anhydrous hexane solution of titanium tetrachloride and then 10 g of water/acetone (1/1 weight ratio).

The charged mass was gradually heated while agitating and distilling off low boiling substances, and the reaction temperature finally reached 300° C. The reaction mass was maintained at that temperature until no distillate appeared. The distillate obtained was analyzed by was chromatography. As the result, it was found that cumene, α-methylstyrene and phenol present in the distillate as decomposition products of the charged dimethylphenyl carbinol, α-methylstyrene dimer, p-cumyl phenol and o-cumyl phenol were recovered with 10, 85 and 85 mol%, respectively. (Cumene is that which is obtained by hydrogenation of α-methylstyrene with hydrogen generated in the reaction system.)

It was found, on assay under X-ray, an electron microscope or the like, that most of the titanium compound present in the residue in the reaction vessel was titanium hydroxide or titanium oxide which had an average particle diameter of 0.5-1.0 μm.

Examples 2-11

In Example 1, in place of the titanium tetrachloride, there were used other metallic compounds as indicated in Table 1. Further, hydrolysis of the metallic compounds used was carried out, without addition of the water/acetone, by the use of water formed by pyrolytic decomposition of dimethylphenyl carbinol, or the metallic compounds used were decomposed to corresponding hydroxides with ammonia formed from an aqueous urea solution added and heated, thereby forming ultrafine oxygen containing metallic compound catalysts.

The results obtained are shown in Table 1.

TABLE 1

| Example | 2 | 3 | 4 | 5 | 6 | 7 | 8 | 9 | 10 | 11 | 12 |
|---|---|---|---|---|---|---|---|---|---|---|---|
| Metallic compound | AlCl$_3$ | SiCl$_4$ AlCl$_3$ | MgCl$_2$. 6H$_2$O | CuCl$_2$ | ZnCl$_2$ | CoCl$_2$ | FeCl$_2$ | NiCl$_2$ | CrCl$_3$. 6H$_2$O | Vanadium chloride | Mn |
| Concentration of metallic compound (concentration of metal based on phenol distillation residue) (ppm by weight) | 100 | Si:65 Al:35 | 1000 | 1000 | 1000 | 50 | 50 | 50 | 100 | 500 | 1000 |
| Yield of cumene (mol %) | 10 | 10 | 15 | 20 | 17 | 15 | 10 | 13 | 16 | 15 | 18 |
| Yield of α-methylstyrene (mol %) | 75 | 70 | 60 | 50 | 60 | 60 | 77 | 78 | 70 | 50 | 6 |
| Yield of phenol (mol %) | 80 | 85 | 70 | 66 | 65 | 75 | 80 | 83 | 78 | 77 | 65 |
| Average particle diameter of catalyst (um) | 0.1 | 0.05 | 0.1 | 0.1 | 0.1 | 0.1 | 0.1 | 0.1 | 0.1 | 0.1 | 0.1 |

Comparative Example 1

The same procedure as described in Example 1 was repeated except that titanium oxide (a product as stipulated in JIS Z8801, passing through a 100 mesh screen) was used in place of the titanium tetrachloride used in Example 1.

The results obtained are shown in Table 2.

Comparative Example 2

The same procedure as described in Example 2 was repeated except that aluminum hydroxide (a product as stipulated in JIS Z8801, passing through a 100 mesh screen) was used in place of the aluminum chloride used in Example 2.

The results obtained are shown in Table 2.

Comparative Example 3

The same procedure as described in Example 3 was repeated except that silica-alumina (a product as stipulated in JIS Z8801, passing through a 100 mesh screen) was used in place of the silicon tetrachloride and aluminum chloride used in Example 3.

The results obtained are shown in Table 2.

TABLE 2

| Comparative Example | 1 | 2 | 3 |
|---|---|---|---|
| Metallic compound | Titanium oxide | Aluminum hydroxide | Silica-alumina |
| Concentration[*1] of metallic compound (ppm by weight) | 1000 | 100 | Si:65 Al:35 |
| Yield of cumene | 20 | 25 | 70 |
| Yield of γ-methylstyrene | 10 | 7 | 10 |
| Yield of phenol | 5 | 10 | 50 |
| Average particle diameter of catalyst (μm) | 120 | 120 | 120 |

[*1] The concentration, based on the phenol distillation residue, of the metallic compound calculated as metal.

Examples 13–18

In Example 1, in place of the titanium tetrachloride used in Example 1, there were used other metallic compounds as indicated in Table 3. Further, hydrolysis of the metallic compounds used was carried out, without addition of the water/acetone by using water formed from pyrolytic decomposition of dimethylphenyl carbinol, thereby forming ultrafine oxygen containing metallic compound catalysts.

The results obtained are shown in Table 3.

TABLE 3

| Example | 13 | 14 | 15 | 16 | 17 | 18 |
|---|---|---|---|---|---|---|
| Organometallic compound | Tetra-n-butyl titanate | Aluminum isopropoxide | Phenyl magnesium bromide | Aluminum phenoxide | Titanium isopropoxide | Aluminum isopropoxide n-butyl magnesium chloride |
| Concentration of organometallic compound (concentration of metal based on phenol distillation residue) (ppm by weight) | 50 | 20 | 30 | 50 | 50 | Al:30 Mg:30 |
| Yield of cumene (mol %) | 10 | 11 | 13 | 12 | 11 | 14 |
| Yield of α-methylstyrene (mol %) | 85 | 80 | 75 | 85 | 80 | 80 |
| Yield of phenol (mol %) | 95 | 85 | 82 | 90 | 88 | 90 |
| Solvent for organometallic compound | — | Benzene | Tetrahydrofuran | Phenol | Benzene | Diethyl ether |
| Particle diameter of catalyst (um) | 0.05 | 0.03 | 0.03 | 0.05 | 0.05 | — |

What is claimed is

1. A process for recovering useful substances from a phenol distillation residue, said process comprising the steps of:
    subjecting said residue to pyrolytic decomposition at a temperature of 200°–250° C. and under a pressure of from 400 mmHg to 4 kgf/cm$^2$abs. in the presence of at least one oxygen-containing metallic compound, as a catalyst, having a particle diameter of 0.002–100 μm, to produce a pyrolytic reaction mixture, said residue resulting from the separation by distillation of phenol, acetone and cumene from a reaction mixture obtained by oxidizing cumene with molecular oxygen to cumene hydroperoxide followed by acid cleavage; and
    recovering useful substances such as cumene, alpha-methylstyrene and phenol from the pyrolytic reaction mixture, said oxygen-containing metallic compound being formed in said phenol distillation residue and selected from the group consisting of hydroxides, hydrated oxides and oxides of metals, excluding alkali metals, belonging to the third and fourth period of the Periodic Table.

2. The process as claimed in claim 1 wherein the pyrolytic decomposition reaction is carried out at a temperature of 250°–300° C.

3. The process as claimed in claim 1 wherein the useful substances recovered thereby are cumene, α-methylstyrene and phenol.

4. The process as claimed in claim 1 wherein the metallic compound catalyst is used in an amount of 0.1–50,000 ppm by weight based on the phenol distillation residue.

* * * * *